(12) United States Patent
Nissan et al.

(10) Patent No.: US 11,998,462 B2
(45) Date of Patent: Jun. 4, 2024

(54) SYSTEMS, METHODS AND DEVICES FOR TREATING TRICUSPID INSUFFICIENCY

(71) Applicant: Innoventric Ltd., Rehovot (IL)

(72) Inventors: Ori Nissan, Yavne (IL); Amir Danino, Rehovot (IL); Yair Pichersky, Hanevi'im (IL)

(73) Assignee: INNOVENTRIC LTD., Rehovot (IL)

( * ) Notice: Subject to any disclaimer, the term of this patent is extended or adjusted under 35 U.S.C. 154(b) by 469 days.

(21) Appl. No.: 17/115,676

(22) Filed: Dec. 8, 2020

(65) Prior Publication Data

US 2021/0085494 A1    Mar. 25, 2021

Related U.S. Application Data (63) Continuation of application No. PCT/IL2019/050658, filed on Jun. 7, 2019.

(Continued)

(51) Int. Cl.
*A61F 2/856*  (2013.01)
*A61F 2/24*  (2006.01)
*A61F 2/90*  (2013.01)

(52) U.S. Cl.
CPC .............. *A61F 2/856* (2013.01); *A61F 2/24* (2013.01); *A61F 2/2412* (2013.01); *A61F 2/90* (2013.01);
(Continued)

(58) Field of Classification Search
CPC .. A61F 2/856; A61F 2/2412; A61F 2002/068; A61F 2/24; A61F 2/2403
See application file for complete search history.

(56) References Cited

U.S. PATENT DOCUMENTS

| 5,957,978 A | 9/1999 | Blom |
| 7,799,072 B2 | 9/2010 | Greenberg |

(Continued)

FOREIGN PATENT DOCUMENTS

| CN | 107212947 A | 9/2017 |
| EP | 2522306 | 11/2012 |

(Continued)

OTHER PUBLICATIONS

International Search Report for International Application PCT/IB2017/050534, dated Jun. 12, 2017.
(Continued)

*Primary Examiner* — William H Matthews
(74) *Attorney, Agent, or Firm* — COOLEY LLP (57) ABSTRACT

Embodiments of the present disclosure are directed to devices and methods for treating tricuspid valve insufficiency. For example, in some embodiments, a tricuspid insufficiency treatment device is provided, and includes a tubular member configured for implantation within a vena cava of a patient, where the tubular member is formed with a sidewall. The device also includes at least two (2) valves arranged circumferentially along the sidewall, where each valve comprises an opening formed in the sidewall, and a blocking member arranged to block and unblock a respective opening of the plurality of openings. Each blocking member comprises a flap or cover pivotally attached at or proximate a portion of a respective opening and arranged to block and unblock the opening during ventricular systole and ventricular diastole, respectively, such that the opening is unblocked in a direction opposite to the attachment of the flap or cover. The at least two valves are arranged along a first circumference at a first location between the ends of the tubular member.

25 Claims, 9 Drawing Sheets

Related U.S. Application Data (60) Provisional application No. 62/682,648, filed on Jun. 8, 2018.

(52) U.S. Cl.
CPC ............... *A61F 2210/0014* (2013.01); *A61F 2220/0075* (2013.01); *A61F 2250/0013* (2013.01)

(56) References Cited

U.S. PATENT DOCUMENTS

| | | | |
|---|---|---|---|
| 8,470,013 | B2 | 6/2013 | Duggal et al. |
| 8,470,018 | B2 | 6/2013 | Hartley et al. |
| 8,636,789 | B2 | 1/2014 | Ivancev et al. |
| 8,870,944 | B2 | 10/2014 | Sochman et al. |
| 10,799,342 | B2 | 10/2020 | Danino |
| 2004/0093070 | A1 | 5/2004 | Hojeibane et al. |
| 2004/0106976 | A1 | 6/2004 | Bailey et al. |
| 2004/0206363 | A1 | 10/2004 | McCarthy et al. |
| 2005/0059923 | A1 | 3/2005 | Gamboa |
| 2005/0060026 | A1 | 3/2005 | Gamboa |
| 2006/0276813 | A1 | 12/2006 | Greenberg |
| 2006/0287712 | A1 | 12/2006 | Eidenschink |
| 2007/0055351 | A1 | 3/2007 | Eidenschink et al. |
| 2007/0156233 | A1 | 7/2007 | Kapadia et al. |
| 2007/0203572 | A1 | 8/2007 | Heuser et al. |
| 2007/0250154 | A1 | 10/2007 | Greenberg et al. |
| 2008/0114446 | A1 | 5/2008 | Hartley et al. |
| 2008/0161901 | A1 | 7/2008 | Heuser et al. |
| 2010/0106240 | A1 | 4/2010 | Duggal et al. |
| 2012/0191180 | A1 | 7/2012 | Hartley et al. |
| 2014/0358221 | A1 | 12/2014 | Ho et al. |
| 2015/0230916 | A1 | 8/2015 | Ivancev et al. |
| 2015/0282958 | A1 | 10/2015 | Centola et al. |
| 2017/0165061 | A1 | 6/2017 | Figulla et al. |
| 2017/0239043 | A1 | 8/2017 | Wei |
| 2018/0021130 | A1* | 1/2018 | Danino ............... A61F 2/07 623/1.13 |
| 2021/0251748 | A1 | 8/2021 | Danino |

FOREIGN PATENT DOCUMENTS

| | | |
|---|---|---|
| EP | 2929860 A1 | 10/2015 |
| JP | 2013518696 A | 5/2013 |
| JP | 2015198914 A | 11/2015 |
| JP | 2019504739 A | 2/2019 |
| WO | WO 2004/093935 A2 | 11/2004 |
| WO | WO 2011/017123 A2 | 2/2011 |
| WO | WO 2011/076408 A1 | 6/2011 |
| WO | WO-2011100290 A1 | 8/2011 |
| WO | WO 2014/107748 A2 | 7/2014 |
| WO | WO 2016/008526 A1 | 1/2016 |
| WO | WO-2016114719 A1 | 7/2016 |
| WO | WO-2017137868 A1 | 8/2017 |
| WO | WO-2019234755 A2 | 12/2019 |

OTHER PUBLICATIONS

Written Opinion issued for International Application PCT/IB2017/050534, dated Aug. 14, 2018.
International Preliminary Report on Patentability issued for International Application PCT/IB2017/050534, dated Aug. 14, 2018.
European Examination Report issued for Application Serial No. EP 17709795.3, dated Jan. 21, 2019.
Response to the European Examination Report dated May 30, 2019, for Application Serial No. EP 17709795.3.
Communication issued for European Application Serial No. EP 17709795.3, dated Dec. 11, 2019.
International Search Report for International Application PCT/IL2019/050658 dated Apr. 7, 2020.
Written Opinion issued for International Application PCT/IL2019/050658 dated Apr. 7, 2020.
International Preliminary Report on Patentability issued for International Application PCT/IL2019/050658 dated Dec. 8, 2020.
Opposition Communication issued for European Application Serial No. EP 17709795.3, dated Mar. 5, 2021 (33 pages).
Opposition Communication issued for European Application Serial No. EP 17709795.3, dated Mar. 12, 2021 (26 pages).
Rutherford et al. "Vascular Surgery", W.B. Saunders Company, 2000, 5th Ed., p. 584-618.
Notice of Opposition issued against EP Patent EP3402440, Proprietor: Innoventric Ltd, Opponent: Medira GmbH, dated Mar. 1, 2021 (5 pages).
Consolidated List of Opposition Documents issued for European Application Serial No. EP 17709795.3, dated Mar. 1, 2021 (1 page).
Notice of Further Opposition to Opponent issued for European Application Serial No. EP 17709795.3, dated Mar. 12, 2021 (2 pages).
Annex to Opposition Letter dated Mar. 1, 2021 (1 page).
Communication of Notices of Opposition issued for European Application Serial No. EP 17709795.3, dated Mar. 12, 2021 (1 page).
Brief Communication—Letter from the Opponent—Opposition Proceedings issued for European Application Serial No. EP 17709795.3, dated May 10, 2022 (12 pages).
Brief Communication—Letter from the Proprietor_Opposition Proceedings issued for European Application Serial No. EP 17709795.3, dated May 10, 2022 (11 pages).
Brief Communication—Opposition Proceedings issued for European Application Serial No. EP 17709795.3, dated Jul. 29, 2021 (63 pages).
Grounds for Appeal filed for European Application Serial No. EP 17709795.3, dated Dec. 7, 2022 (37 pages).
Information about the Results of Oral Proceedings, Opposition issued for European Application Serial No. EP 17709795.3, dated Jul. 5, 2022 (12 pages).
International Search Report and Written Opinion for International Application No. PCT/IB2022/051347 dated May 11, 2022, 9 pages.
No Author, "Trying | Tubectomy" The American Heritage Dictionary of the English Language, Fourth Edition, 2006, 3 pages.
No Author, "TTS | Tubuai Islands", Angus Stevenson, Ed., Oxford Dictionary of English, Third Edition, 2010, 3 pages.
Noorani et al. "Valve-in-valve procedure: importance of the anatomy of surgical bioprostheses", MultiMedia Manual of Cardio-Thoracic Surgery, 2014, 8 pages.
Notice of Appeal filed for European Application Serial No. EP 17709795.3, dated Oct. 7, 2022 (2 pages).
Office Action for Japanese Application No. JP20200568467 dated Jul. 3, 2023, 13 pages.
Patil et al. "Assessment of inferior vena cava diameter by echocardiography in normal Indian population: A prospective observational study", Indian Heart Journal 68 (2016), S26-S30.
Reply of the Patent Proprietor to the Notice of Opposition issued for European Application Serial No. EP 17709795.3, dated Jul. 22, 2021 (19 pages).
Reply to Appeal filed for European Application Serial No. EP 17709795.3, dated Apr. 20, 2023 (43 pages).
Taneja et al. "Normative Data for IVC Diameter and its Correlation with the Somatic Parameters in Healthy Indian Children", Indian Journal of Pediatry, Feb. 2018, 85(2):108-112.
Transmittal of Decision and Current State of Proceedings issued for European Application Serial No. EP 17709795.3, dated Nov. 24, 2021 (15 pages).
Transmittal of Interlocutory Decision and Current State of Proceedings issued for European Application Serial No. EP 17709795.3, dated Jul. 28, 2022 (69 pages).
Written Submission in Preparation to/during Oral Proceedings issued for European Application Serial No. EP 17709795.3, dated May 4, 2022 (19 pages).

\* cited by examiner

Section A-A

SYSTEMS, METHODS AND DEVICES FOR TREATING TRICUSPID INSUFFICIENCY

RELATED APPLICATIONS

The present application is a bypass continuation application under 35 USC § 111(a) of PCT/IL2019/050658, having an international filing date of 7 Jun. 2019, and also claims priority to and benefit of U.S. provisional patent application No. 62/682,948, filed Jun. 8, 2018. Embodiments of the present disclosure are also related to PCT application no. PCT/IB2017/050534, filed 1 Feb. 2017, entitled, "Treatment of Tricuspid Insufficiency", and U.S. provisional patent application No. 62/292,422, filed Feb. 8, 2016. The disclosure for each of the applications listed above is herein incorporated by reference in its entirety.

FIELD OF INVENTION

The present invention generally relates to medical systems, apparatuses, devices, and methods for implantation in the heart thereof, and particularly, but not only, to a stent based device for treating an incompetent or regurgitant tricuspid (atrioventricular) valve.

BACKGROUND

The tricuspid valve prevents back flow of blood from the right ventricle into the right atrium when it closes during ventricular systole and allows blood to flow from right atrium into right ventricle when it opens during ventricular diastole.

An insufficient tricuspid valve causing tricuspid regurgitation (TR) may occur from tricuspid annular dilation and right ventricular enlargement. TR is often secondary to left heart failure from myocardial or valvular causes, right ventricular volume or pressure overload and dilation of cardiac chambers. TR causes right atrial overload that is transmitted to the superior and inferior vena cava (SVC, IVC) and their tributaries. Eventually, this leads to hepatic congestion, ascites, anasarca, peripheral edema and other clinical symptoms of congestive heart failure. If untreated, significant tricuspid regurgitation frequently leads to heart failure and death.

Clinically available treatments for TR are open heart surgery or medication. However, open heart surgery for the replacement/repair of the tricuspid valve is rarely carried out, mainly due to its high mortality and morbidity rates. Medication, on the other hand, may not solve the problem and allows the disease to progress, leaving the patients with a deteriorated quality of life and cardiac function.

Due to the high surgical risk of tricuspid valve replacement/repair, currently, the vast majority of TR patients are deemed inoperable. This results in an extremely large number of untreated patients with significant TR.

SUMMARY OF SOME OF THE EMBODIMENTS

Accordingly, in some embodiments, a tricuspid insufficiency treatment device is provided, and includes a tubular member configured for implantation within a vena cava of a patient, where the tubular member is formed with a sidewall. The device also includes at least two (2) valves arranged circumferentially along the sidewall, where each valve comprises an opening formed in the sidewall, and a blocking member arranged to block and unblock a respective opening of the plurality of openings. Each blocking member comprises a flap or cover pivotally attached at or proximate a portion of a respective opening and arranged to block and unblock the opening during ventricular systole and ventricular diastole, respectively, such that the opening is unblocked in a direction opposite to the attachment of the flap or cover. The at least two valves are arranged along a first circumference at a first location between the ends of the tubular member.

Such embodiments can further include at least one of (and in some embodiments, a plurality of, and in some embodiments substantially all of) the following additional structure, features, steps, functionalities, and/or clarifications, yielding yet other embodiments (moreover, each of the items in the listing below, and combinations of the items listed below can be stand-alone embodiments):

a third valve which can be arranged on a second circumference spaced closer to one of the ends of the tubular member than that of the two (2) valves arranged on the first circumference;

the at least two (2) valves can be configured to be only three (3) valves;

the tubular member and the blocking members of the valves can be configured to form a closed cylindrical outer shape when each blocking member blocks a respective opening;

a covering which can be configured to at least a portion of the tubular member;

the covering can be configured to not cover the openings;

the covering can be configured to additionally cover each blocking member;

each of the first and second valves can be hinged or otherwise attached to the tubular member on opposite sides such that each blocking member opens away from the other blocking member;

a third valve of the plurality of valves can be hinged or otherwise attached such that the blocking member opens away from the first and second blocking member;

the tubular member can include an expandable stent having a plurality of cells, wherein each of the plurality of valves corresponds to a specific cell of the stent;

at least one of: each of the openings and each of the cells accommodating a respective opening includes a rhombus shape;

the stent can comprise a corona stent, where:
the corona stent includes at least one of: a first inferior vena-cava (IVC) portion, a second superior vena-cava (SVC) portion, and a third central portion arranged between the IVC portion and the SVC portion;

each blocking member can include a shape memory reinforcing wire therein or thereon, where the reinforcing wire can be arranged at or near at least a portion of the perimeter of the blocking member, where the reinforcing wire can be arranged at or near substantially the entire perimeter of the blocking member;

a single side of the blocking member can be attached to the tubular member, via, for example, suturing;

a skirt, where the skirt can be arranged on and/or otherwise attached to a portion of the tubular member, and can be configured to at least one of preventing backflow from the right atrium (RA) into the inferior vena-cava (IVC), so as to redundify graft covering of the IVC member, and preventing blockage of one or more hepatic veins;

the skirt can comprise at least one of a fabric and a reinforcement;

the skirt can comprise a fabric and a reinforcement, where the reinforcement can comprise a shape memory wire;

the wire can be arranged along at least a portion of the perimeter of the skirt;

the wire can be arranged along a majority of the perimeter of the skirt;

a covering, which can be attached to the tubular member and/or stent via a plurality of sutures;

and the tubular member can include a longitudinal axis, where at least one of the plurality of valves, and/or the device as a whole, can be configured so as to cause substantially all the blood flowing out therefrom to flow in a non-perpendicular direction relative to at least the longitudinal axis and the vena cava.

Accordingly, in some embodiments, a tricuspid insufficiency treatment device or device (which may also be referred to as an apparatus or a system) is provided and includes a tubular member configured for implantation within a vena cava of a patient, where the tubular member includes a stent and formed with a sidewall, and the stent includes a plurality of open cells, and is expandable (in some embodiments, self-expandable). The device further includes at least three (3) valves arranged circumferentially along the sidewall, where each valve comprising an opening (which may also be referred to as a fenestrations or an aperture) formed in the sidewall, and a blocking member arranged to block and unblock a respective opening of the plurality of openings. Each blocking member includes a reinforcing wire arranged therein and/or thereon, and comprises a flap or cover pivotally attached at or proximate a portion of a respective opening and arranged to block and unblock the opening during ventricular systole and ventricular diastole, respectively, such that the opening is unblocked in a direction opposite to the attachment of the flap or cover. The device also includes a first and a second valve of the at least three (3) valves are arranged along a first circumference at a first location between the ends of the tubular member, and a third valve of the three (3) valves is arranged on a second circumference spaced closer to one of the ends of the tubular member than that of the two (2) valves arranged on the first circumference. Each of the first and second valves is hinged to the tubular member on opposite sides such that each blocking member opens away from the other blocking member. In some embodiments, the stent includes a plurality of cells, and each of the plurality of valves corresponds to a specific cell. The device further includes a covering attached to the tubular member via a plurality of sutures and configured to cover at least a portion of at least one of: the sidewall and the stent, save for the openings, and a skirt including a reinforcing wire therein and/or thereon. The skirt is arranged on and attached to a portion of the tubular member and configured to at least one of preventing backflow from the right atrium (RA) into the inferior vena-cava (IVC), so as to redundify graft coverage of the IVC member, and preventing blockage of one or more hepatic veins.

Such embodiments can further include at least one of (and in some embodiments, a plurality of, and in some embodiments substantially all of) the following additional structure, features, steps, functionalities, and/or clarifications, yielding yet other embodiments (moreover, each of the items in the listing below, and combinations of the items listed below can be stand-alone embodiments):

the covering can be configured to additionally cover each blocking member;

the tubular member and the blocking members of the valves can be configured to form a closed cylindrical outer shape when the blocking member blocks the opening;

at least one of the: each of the openings and each of the cells accommodating a respective opening, can include a rhombus shape;

the stent can comprise a corona stent;

the corona stent can include a first inferior vena-cava (IVC) portion, a second superior vena-cava (SVC) portion, and a third central portion arranged between the IVC portion and the SVC portion;

the reinforcing wire can comprise a shape memory reinforcing wire;

the reinforcing wire can be arranged at or near at least a portion of the perimeter of the blocking member;

the reinforcing wire can be arranged at or near substantially the entire perimeter of the blocking member;

a single side of each blocking member can be attached to the tubular member;

the blocking member can be attached via suturing;

reinforcement wire of the skirt can comprise a shape memory wire;

the wire can be arranged along at least a portion of the perimeter of the skirt;

the wire can be arranged along a majority of the perimeter of the skirt;

the covering can be attached to the tubular member and/or stent via a plurality of sutures;

and the tubular member can include a longitudinal axis, where at least one of the plurality of valves, or the device as a whole, can be configured so as to cause substantially all the blood flowing out therefrom to flow in a non-perpendicular direction relative to at least the longitudinal axis and the vena cava.

In some embodiments, a tricuspid insufficiency treatment device is provided and includes a tubular member configured for implantation within a vena cava of a patient and formed with a sidewall. The device also includes at least three (3) valves arranged circumferentially along the sidewall, where each valve comprises an opening formed in the sidewall, and a blocking member comprising a flap or cover pivotally attached at or proximate a portion of a respective opening and arranged to block and unblock the opening during ventricular systole and ventricular diastole, respectively, such that the opening is unblocked in a direction opposite to the attachment of the flap or cover. A first and a second valve of the at least three (3) valves are arranged along a first circumference at a first location between the ends of the tubular member, and a third valve of the three (3) valves is arranged on a second circumference spaced closer to one of the ends of the tubular member than that of the two (2) valves arranged on the first circumference.

Such embodiments can further include at least one of (and in some embodiments, a plurality of, and in some embodiments substantially all of) the following additional structure, features, steps, functionalities, and/or clarifications, yielding yet other embodiments (moreover, each of the items in the listing below, and combinations of the items listed below can be stand-alone embodiments):

the at least three (3) valves can comprise only three (3) valves;

the tubular member and the blocking members of the valves can form a closed cylindrical outer shape when each blocking member blocks a respective opening;

a covering can be included and configured to at least a portion of the tubular member;
   the covering need not cover the openings, and
   the covering can be configured to additionally cover each blocking member;

each of the first and second valves can be hinged or otherwise attached to the tubular member on opposite sides such that each blocking member opens away from the other blocking member;

the third valve of the plurality of valves can be hinged or otherwise attached such that the blocking member can open away from the first and second blocking member;

the tubular member can include an expandable stent having a plurality of cells, where each of the plurality of valves can corresponds to a specific cell of the stent;
   at least one of the: each of the openings and each of the cells accommodating a respective opening can be rhombus shaped;

if a stent is included, the stent can comprise a corona stent, where the corona stent can comprise or otherwise include any one or more of: a first inferior vena-cava (IVC) portion, a second superior vena-cava (SVC) portion, and a third central portion arranged between the IVC portion and the SVC portion;

each blocking member can include a shape memory reinforcing wire therein or thereon;
   the reinforcing wire can be arranged at or near at least a portion of the perimeter of the blocking member;
   the reinforcing wire can be arranged at or near substantially the entire perimeter of the blocking member;

a single side of the blocking member can be attached to the tubular member;

each blocking member can be attached via suturing;

a skirt can be included, where the skirt can be arranged on and attached to a portion of the tubular member and can also configured to at least one of prevent backflow from the right atrium (RA) into the inferior vena-cava (IVC), so as to redundify graft covering of the IVC member, and preventing blockage of one or more hepatic veins.
   the skirt can comprise at least one of a fabric and a reinforcement, where the reinforcement can comprise a shape memory wire, and the wire can be arranged along at least a portion of the perimeter of the skirt, or, wire can be arranged along a majority of the perimeter of the skirt;

if a covering is included, the covering can be attached to the tubular member and/or stent via a plurality of sutures;

and the tubular member can include a longitudinal axis, and, in some embodiments, at least one of the plurality of valves, or the device as a whole, can be configured so as to cause substantially all the blood flowing out therefrom to flow in a non-perpendicular direction relative to at least the longitudinal axis and the vena cava.

Some embodiments of the disclosure are directed to methods of treating tricuspid valve insufficiency. Specifically, in some embodiments, a method for treating tricuspid valve insufficiency is provided and includes providing a device according to any of the devices disclosed herein, and positioning the device in or adjacent the right atrium of a patient such that a portion is arranged adjacent the superior vena cava, and an opposed portion is arranged adjacent the inferior vena cava. In some embodiments, the device is positioned via the patient's vasculature.

It should be appreciated that all combinations of the foregoing concepts and additional concepts discussed in additional detail below (provided such concepts are not mutually inconsistent) are contemplated as being part of the inventive subject matter disclosed herein. In particular, all combinations of subject matter appearing anywhere in this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION OF SOME OF THE EMBODIMENTS

Figure 1A:
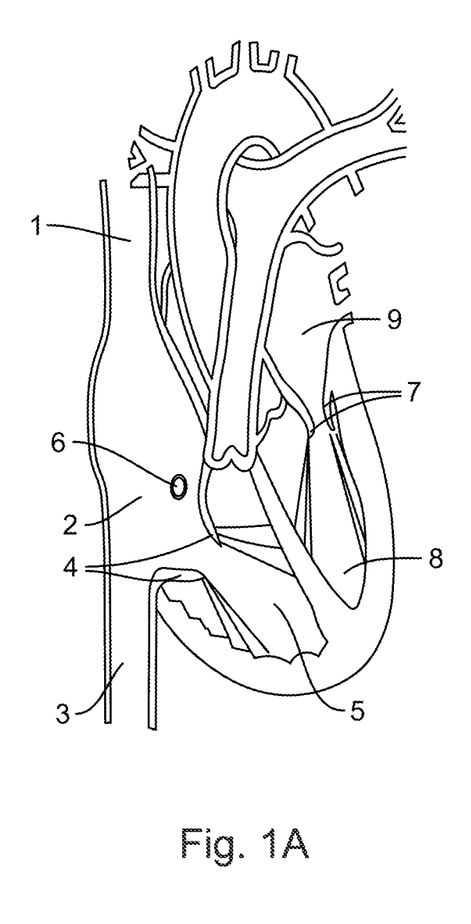
FIGS. 1A and 1B are simplified illustrations of a heart at diastole (FIG. 1A) and ventricular systole (FIG. 1B), respectively, wherein during ventricular systole, the tricuspid valve is not properly closed (FIG. 1B), such that there is tricuspid regurgitation.
Figure 1B:
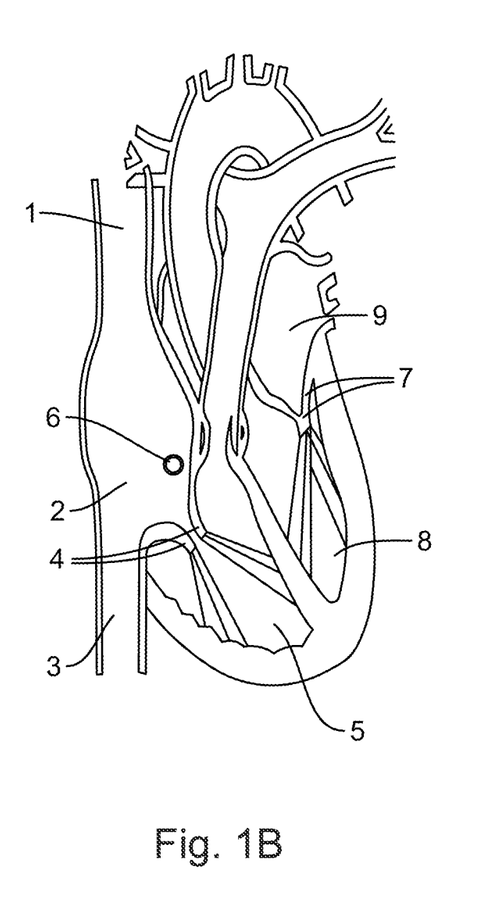

FIGS. 1A-B provide simplified illustrations of a heart at diastole and ventricular systole, respectively, wherein during ventricular systole, the tricuspid valve 4 is not properly closed, such that there is tricuspid regurgitation, according to some embodiments. The superior vena cava 1 returns blood from the upper half of the body, and opens into the upper and back part of the right atrium 2 via a valve-less orifice which is directed downward and forward. The inferior vena cava 3, typically larger than the superior, returns blood from the lower half of the body, and opens into the lowest part of the atrium 2, near the atrial septum. Its orifice is directed upward and backward, and protected by the inferior vena cava valve (called the Eustachian valve). The tricuspid valve 4 is located between the right atrium 2 and the right ventricle 5.

The coronary sinus 6 opens into the right atrium 2, between the orifice of the inferior vena cava and the atrioventricular opening. It returns blood from the substance of the heart and is protected by a semicircular valve, the valve of the coronary sinus (also called the valve of Thebesius). The mitral valve 7 is between the left ventricle 8 and the left atrium 9.

Ventricular systole induces increased pressure in the right and left ventricles 5 and 8. Pressure in the ventricles rises to a level above that of the atria 2 and 9, thus closing the tricuspid and mitral valves 4 and 7. FIG. 1B shows a tricuspid valve 4 being not properly closed, such that there would be tricuspid regurgitation.

FIGS. 2A-F show example schematic illustrations of tricuspid insufficiency treatment devices, according to some embodiments. Each comprises a tubular member/structure 10 configured for implantation into the vena cava (which may also be referred to as the vena cava member 12, or tubular member 12; it will be appreciated that in some embodiments, the body of the device 10 may not be tubular) which can include one or more valves, each comprising, for example, a blocking member 16, and an opening/opening/opening 14 (such terms used interchangeably). The blocking member may be a flap (which may also be referred to as a cover) configured to open up the opening in a sidewall of the device 10/tubular member 12, and close the opening (e.g., at least to fluid passing therethrough), respectively. The blocking member/opening valve(s) combination is configured to allow blood to flow out of the openings during ventricular diastole (the blood being received by ends of the device from the vena cava) when the device is implanted into the vena cava.

As noted, treatment device 10 includes a tubular member 12 implantable in the superior vena cava (SVC) and/or inferior vena cava (IVC). The side wall of tubular member 12 can be formed with an opening(s) 14 (e.g., right atrium openings) and also includes a blocking member 16 arranged to block and unblock the opening 14. As also noted, for example, the blocking member 16 may be a flap valve, in which blocking member 16 is a flap or cover pivoted to a portion of tubular member 12 to block/unblock the opening; in some embodiments, the blocking member is arranged or otherwise affixed at or near an opening, preferably (in some embodiments) on a portion of the perimeter of the blocking member. Such affixation can be via sutures (e.g., see ref no. 19, FIGS. 2D, 2F). The blocking member can open outwards away from the side wall of the tubular member, or in other embodiments, can open sideways or other directions.

The blocking member 16 can be normally open (e.g., FIG. 2A) or normally close with respect to the/a respective opening(s) 14. The mechanism of a normally open or closed blocking member can be of further assistance in controlling the degree of regurgitation or stenosis, respectively. For example, a normally open blocking member requires a certain measurable and controlled closing force. Thus, a normally open blocking member can create a measurable and controlled level of regurgitation. Conversely, a normally closed blocking member can create a measurable and controlled level of stenosis.

The device, according to some embodiments, can be implanted so that the opening(s) 14 is aligned with (faces in a direction of) the orifice of the SVC or with the orifice of the IVC or it can face in other directions, such as sideways (anteriorly/posteriorly). Thus, the blocking member 16 may have its open portion (opening 14) directed towards the superior, inferior, anterior or posterior part of the right atrium.

Figure 2A:
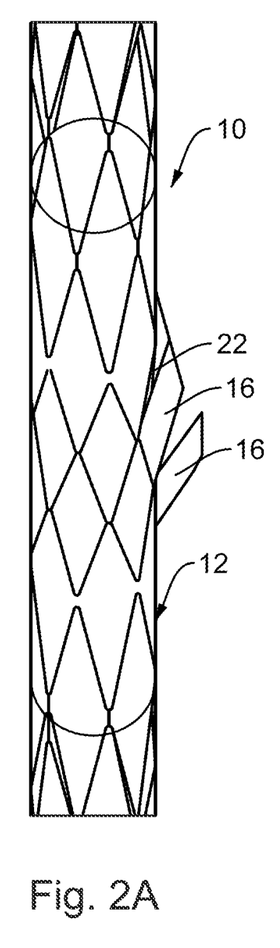
FIGS. 2A-F are simplified schematic illustrations of tricuspid insufficiency treatment devices with one or more valves, according to some embodiments, including illustrating the slight open position of diamond/rhombus shaped valve(s) (FIGS. 2A, 2F) according to some embodiments, a circular/elliptical valve(s) (FIGS. 2B-C) according to some embodiments, a pair (at least) of oblong circular shaped valves (FIG. 2D) according to some embodiments, and a large circular valve device (FIG. 2E) according to some embodiments.
Figure 2B:
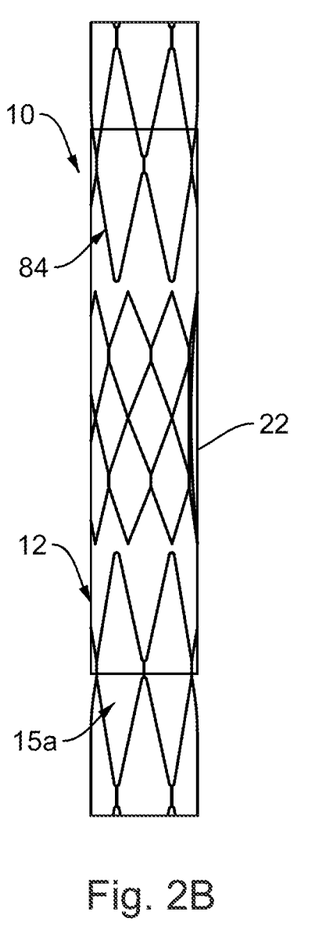

In FIG. 2A, a plurality of (in some embodiments, two, in some embodiments, two or more, in some embodiments, three, and in some embodiments, three or more) openings 14 and corresponding blocking members 16 are provided. For example, a blocking member 16 may be configured (e.g., sized and shaped) such that the blocking member 16 can fit within in a respective opening 14 and block the opening when the tricuspid insufficiency treatment device 10 is in the closed position.

In some embodiments (see, for example, FIG. 2B-C), a single opening may be associated with a one or, in some embodiments, a plurality of blocking members, each blocking member configure to cover a portion of the single opening. In such embodiments, the tricuspid insufficiency treatment device 10, being in the closed position corresponds to the plurality of blocking members configured to fit with each other such that the combined blocking member blocks or covers at least a substantial part of the single opening (including, for example, the entirety of the single opening). In other words, one or more of the blocking members may be integral with one another configured to unitarily block one (or a plurality of) opening(s). For example, the blocking members shown in FIGS. 2A-F, as well as FIGS. 3A-B, can be configured to block a single opening 14 (e.g., three blocking members 16), or such blocking members can be configured to block a plurality of opening. In the illustrations, each opening can be shaped as a parallelogram/diamond/rhombus, for example, where, for example, in some embodiments, the three blocking members swing open to create one large opening (in some embodiments), or open three-individual openings (in some embodiments). In the single or one-opening embodiments, the blocking member together come together and fit with each other to block the entire opening as a unit (e.g., FIG. 2C, 2E). Thus, it is noted that, in some embodiments, an opening can be associated with any number of blocking members, and in some embodiments, blocking members can include any kind of shape, in particular shapes suitable for closing off the opening during systole when the tricuspid insufficiency treatment device 10 is implanted in the vasculature.

The treatment device according to some embodiments, e.g., with multiple flap/blocking member valves, significantly improve the chances of an efficient and safe blood flow, with respect tissue ingrowth, thrombi or other causes of device deterioration.

In some embodiments, the tubular member 10 may be/include a stent 15, which can be self-expanding (e.g., shape memory alloy, polymer and the like) or balloon expandable (e.g., steel alloys, polymers and the like). A blocking member(s) 16 may be made from the same material as the tubular member (e.g., covering the stent) or from other graft materials (e.g., pericardium, porcine valve material, PE material). For example, an opening 14 can be an opening formed when a sidewall of the tricuspid insufficiency treatment device 10 is incised in a semi-circular manner without removing any part of the cut sidewall. In such embodiments, the flap valve that is formed due to the incision (and remains attached or coupled to the tricuspid insufficiency treatment device 10 via a part of the sidewall itself) may serve as a blocking member 16 for the opening 14.

In some embodiments, the stent includes a plurality of open cells which are covered with material (forming the tubular member and/or sidewall thereof). At least one of the cells can be configured to perform as the opening, and the covering (or other suitable material) is hinged or otherwise attached along at least a portion of a perimeter thereof to perform as the blocking member to cover the at least one cell (e.g., see incision embodiments above), and allow blood to flow out of the at least one cell during respective points in the cardiac cycle.

Figure 2C:
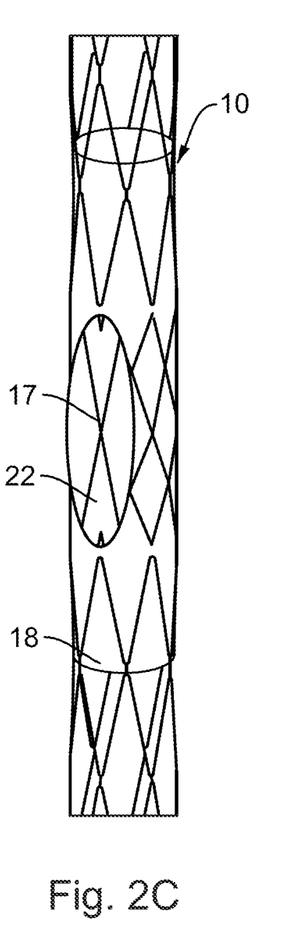
Figure 2D:
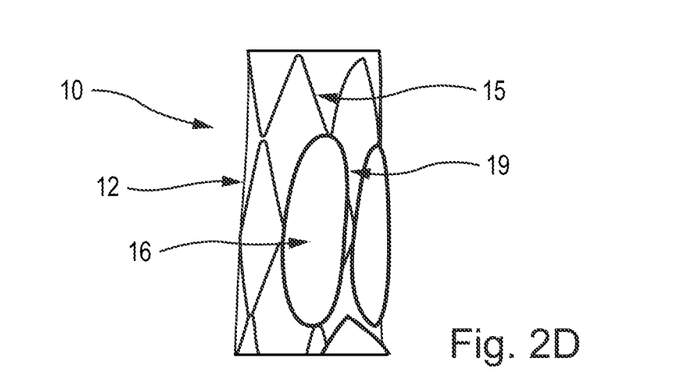
Figure 2E:
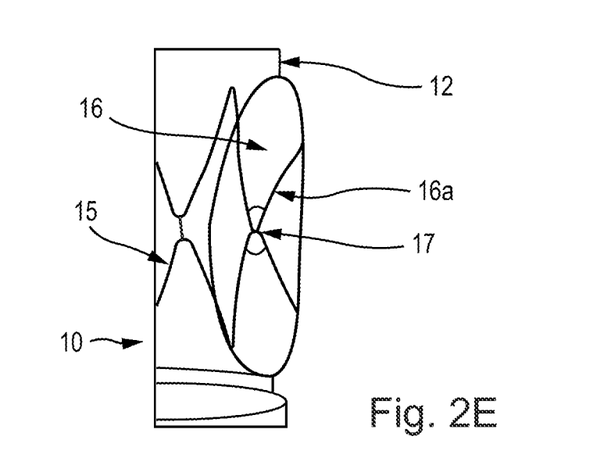
Figure 2F:
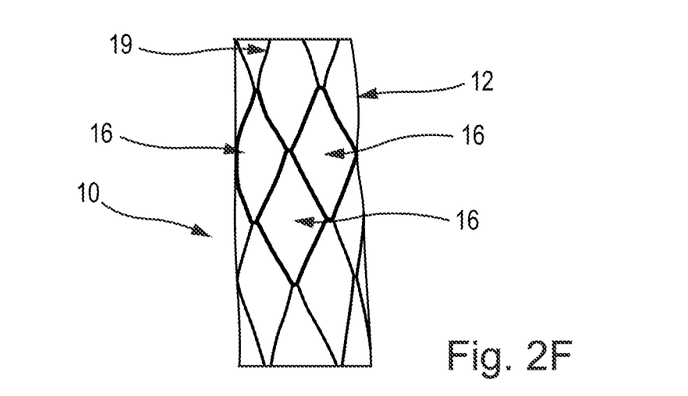

In some embodiments, the stent can be covered by a fabric or other material (e.g., pericardium) 18, and in such embodiments, the blocking member 16 may be a fabric valve (and/or may be pericardium as well). For example, as shown in FIG. 2C, the blocking member 16 may be a flat valve 22 configured for opening up during systole when the tricuspid insufficiency treatment device 20 is implanted in the vasculature. In some embodiments, the blocking element 22 may be a single element covering the entire opening 14 or it may be composed of a plurality of elements that come and fit together during systole to cover the opening entirely or at least substantially entirely. Again, according to some embodiments (e.g., FIG. 2C), the blocking-member can cover one or more openings/openings (e.g., one or more cells in the stent), and be, for example, centrally attached at 17 (for example) within the center of the opening(s). Thus, a portion, and in some embodiments, a substantial portion (or all) of the perimeter of the blocking-member can open from multiple angles to allow blood to flow out therefrom.

In some embodiments, the blocking member may be free of, or include, reinforcing 16a structure, such as wires, rods, tubes, sutures or a mesh. The covering (including the material used for blocking members), may be immersed, sprayed or covered by anti-coagulant agents, anti-platelet agents, tissue growth accelerating or inhibiting agents, antibiotics, statins, anti-inflammatory agents and other materials or medications. The stent structure may include, without limitation, stent rings, independent or interconnected, a braided or laser-cut mesh, a braided or laser cut tubular structure, and/or struts (and/or the like). The insufficiency device/device according to some embodiments may be fixed in-situ, for example, by the radial force of the expandable members, barbs, diverging tubular member ends, stent or other members deployed in the tributaries, or other suitable means. Any subsequent tissue growth on the device may also help in fixation.

The blocking member may be connected to the vena cava/tubular member by any suitable means (including, e.g., integrally therewith, see paragraph [0032]), such as but not limited to, sutures, adhesives, polymer embedding, welding, ultrasonic welding, a unified graft and blocking member material, and others. In some embodiments, the blocking member may be coupled or attached to the tricuspid insufficiency treatment device/device (or sidewall thereof) in a manner that allows for the seamless opening and closing of an tricuspid insufficiency treatment device during diastole and systole, respectively, when the device 10 is implanted in the vasculature. For example, the blocking member may be connected to a sidewall of the device 10 via any one or more of connection or joint types. For example, the coupling, joint or attachment between the blocking member 16 and the sidewall may be in the form of a hinge (via a ring or similar element), a pivot, etc. In some embodiments, the joint may be a weakened articulation between the blocking member and the sidewall that serves as an axis about which the blocking member can swing open during diastole.

The tubular member may be generally cylindrical, which may be referred to as tubular as having been recited (both terms used interchangeably throughout), but alternatively may be non-cylindrical. The term "cylindrical" as used throughout the specification and claims includes not only a circular cross-section, but also elliptical and other curved cross-sections. The diameter of tubular member, according to some embodiments, may be uniform over its axial length. Alternatively, the diameter of tubular member, according to some embodiments, may vary over its axial length. The blocking member may, according to some embodiments, have a triangular shape with rounded corners as shown. Alternatively, it may have an oval, rectangular, circular or other shape, for example, rhombus shaped (according to some embodiments).

Figure 3A:
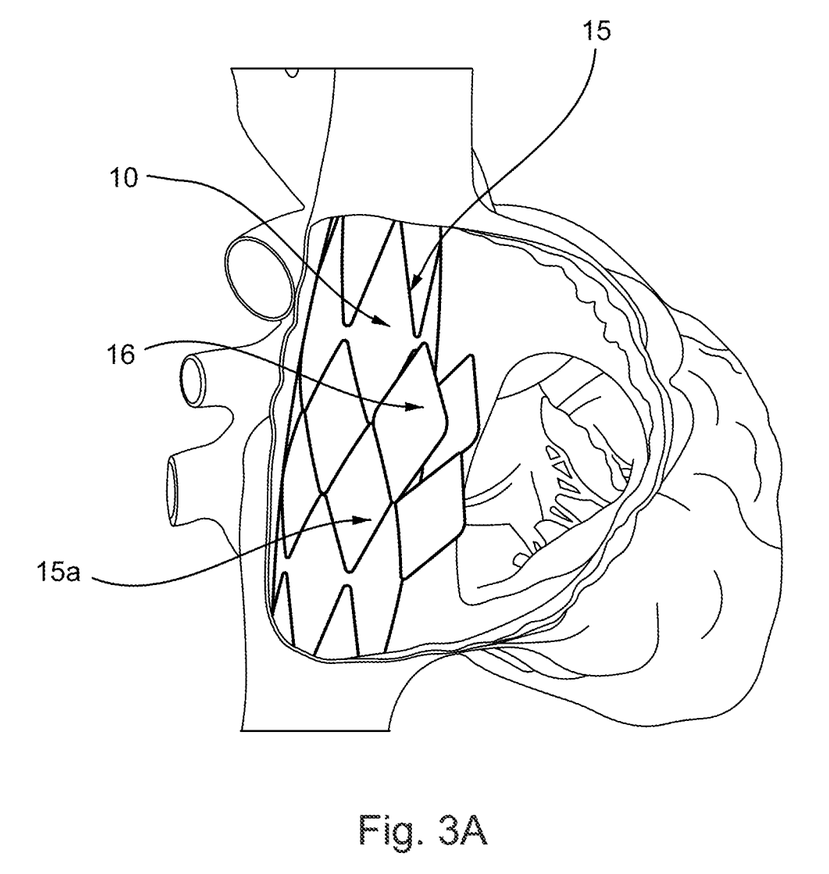
FIGS. 3A and 3B are simplified perspective illustrations of a tricuspid insufficiency treatment device implanted in the vasculature, respectively in diastole (FIG. 4A) and systole (FIG. 4B), according to some embodiments.
Figure 3B:
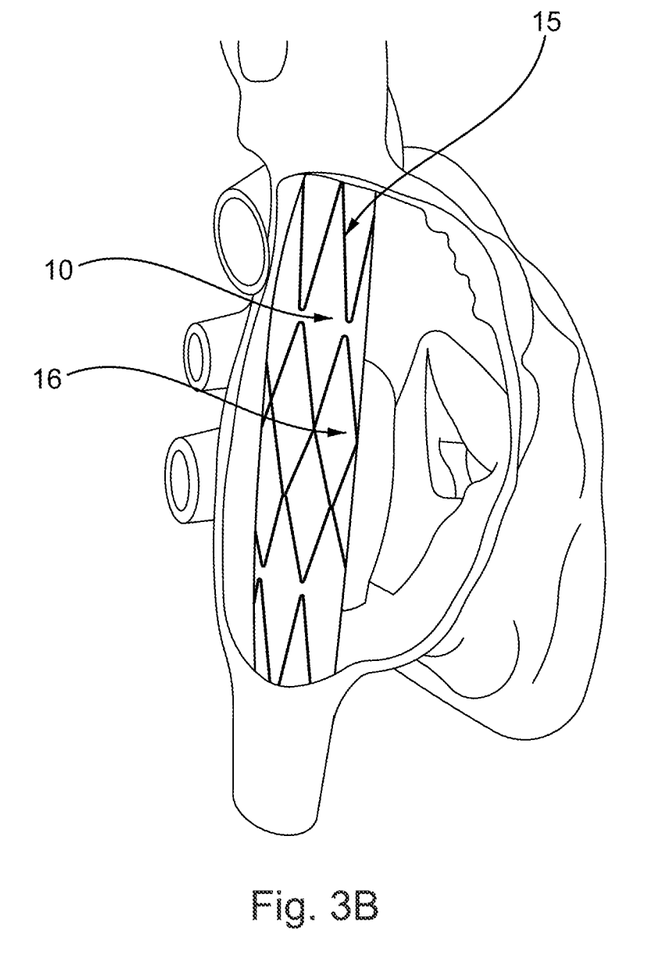

FIGS. 3A-B are simplified illustrations of the tricuspid insufficiency treatment device 10 implanted in the vasculature (e.g., vena cava), respectively in diastole and systole, according to some embodiments. FIG. 3A shows diastole, in which the pressure in the right ventricle drops (e.g., in some embodiments, to about 0 mm Hg) and the blood pressure in the vena cava causes the blocking member(s) 16 to open and allow flow through the opening 14. Systole is shown in FIG. 3B, in which the pressure in the right ventricle increases. Use of the device 10 is due to, in some embodiments, an inadequate tricuspid valve not completely preventing back flow of blood from the right ventricle into the right atrium (i.e., because it cannot close completely). Accordingly, with the device according to some embodiments, the systole pressure causes the blocking member to close and prevent flow through the right atrium opening (see FIG. 3B). This substantially diminishes back flow of blood from the right ventricle and atrium into the venous system. In some embodiments, and as shown in FIG. 3B, when blocking member 16 blocks opening 14, the tubular member and the blocking member together include a closed cylindrical outer shape, which is advantageous for sheathing and un-sheathing the device in a delivery catheter.

Figure 4A:
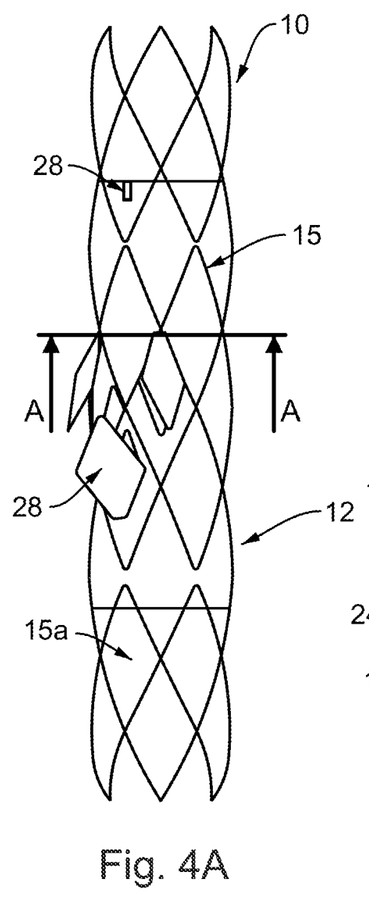
FIGS. 4A-C are simplified illustrations of a tricuspid insufficiency treatment device according to some embodiments, illustrating a side view during diastole (FIG. 4A), perspective view during diastole (FIG. 4B), and a cross-section A-A (FIG. 4C).
Figure 4B:
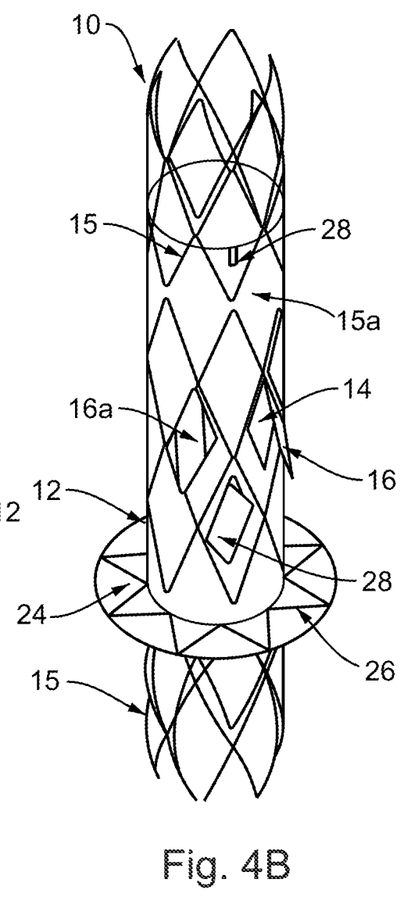
Figure 4C:
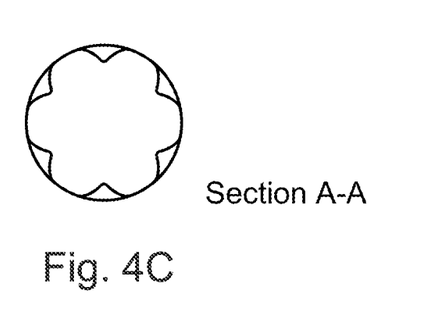

FIGS. 4A-4C illustrate some embodiments of the tricuspid insufficiency device of the present disclosure. As shown, device 10 includes tubular member 12, which can comprise a stent 15, which can include a plurality of cells 15a, and covering 18, and a plurality of valves comprising a blocking member 16 for blocking and unblocking an opening 14. In some embodiments, the opening for one or more of the valves can correspond to only a portion of the area of a cell 15a of the stent (as shown, for example). As shown in the figures, the ends of the stent can be curved slightly, so as to avoid interaction with the interior surface of the vena cava.

Additionally:
  the covering 18 can cover substantially all of the stent, or a portion. Thus, for example, in some embodiments, a portion of the stent at one or more ends (as illustrated, both ends) can be left without a covering; and/or
  radio-opaque markers 28 (see FIG. 4A-B) may be provided on the device for axial and rotational positioning within the body lumen. Typically, radio-opaque markers can be in the shape of the letters 'L', 'E' or 'C' to mark the rotational position of the device, these or other markers can be placed on various axial positions on the device, so that the implanting operator can understand and control the device axial position.

Also, the device illustrated in FIGS. 4A-C can also include a skirt 24, which can include a reinforcing wire 26 therein and/or thereon (which can be arranged in an undulating/sinusoidal configuration, for example, in some embodiments). The skirt can be arranged on and attached to a portion of the tubular member and configured to at least one of prevent backflow from the right atrium (RA) into the inferior vena-cava (IVC), and prevent blockage of one or more hepatic veins.

Figure 5:
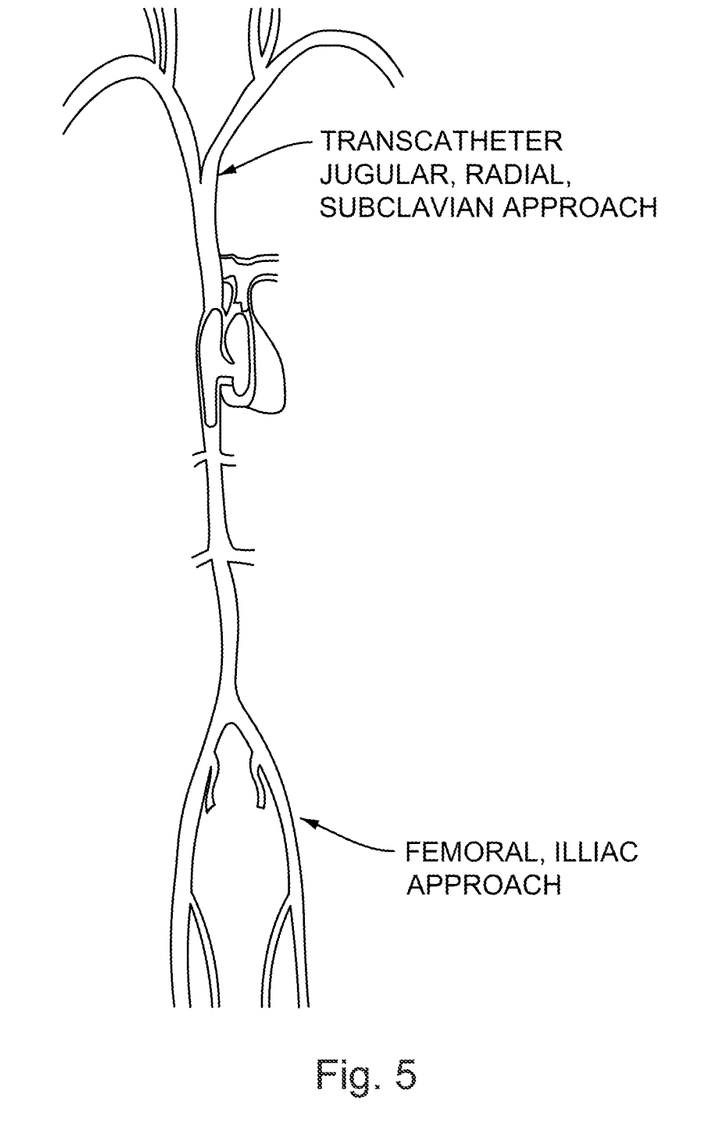
FIG. 5 is a simplified illustration of a percutaneous venous path for implantation of device embodiments of the disclosure, illustrating implantation via lower or upper extremities, according to some embodiments.

The device may be delivered percutaneously or by surgical means. For example, as shown in the example embodiment of FIG. 5, the device may be delivered percutaneously through the IVC in a transcatheter femoral/iliac approach, or through the SVC in a transcatheter jugular/radial/subclavian approach.

Figure 6A:
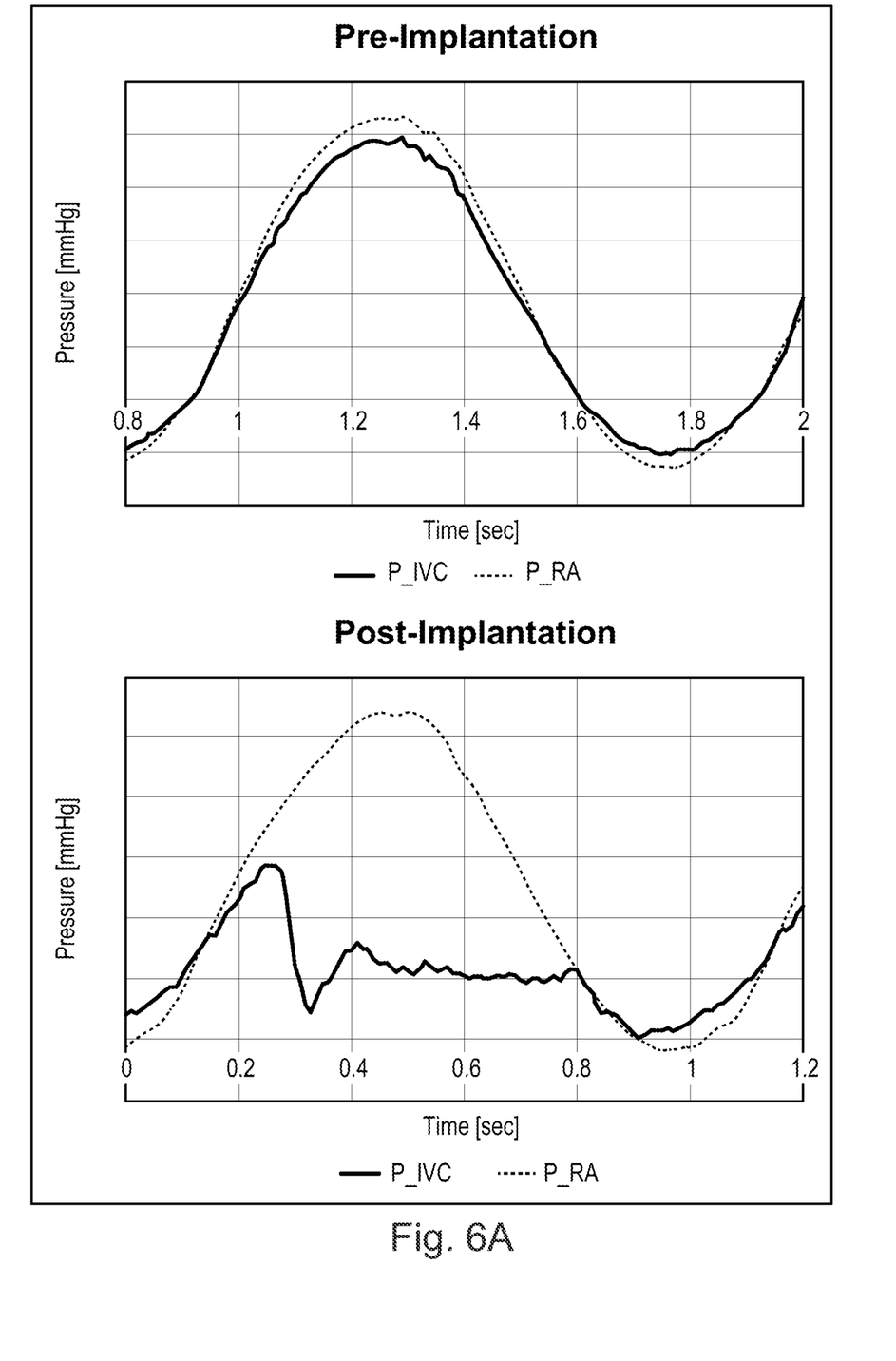
FIGS. 6A and 6B are charts illustrating physiological improvements with respect to post-implantation studies.
Figure 6B:
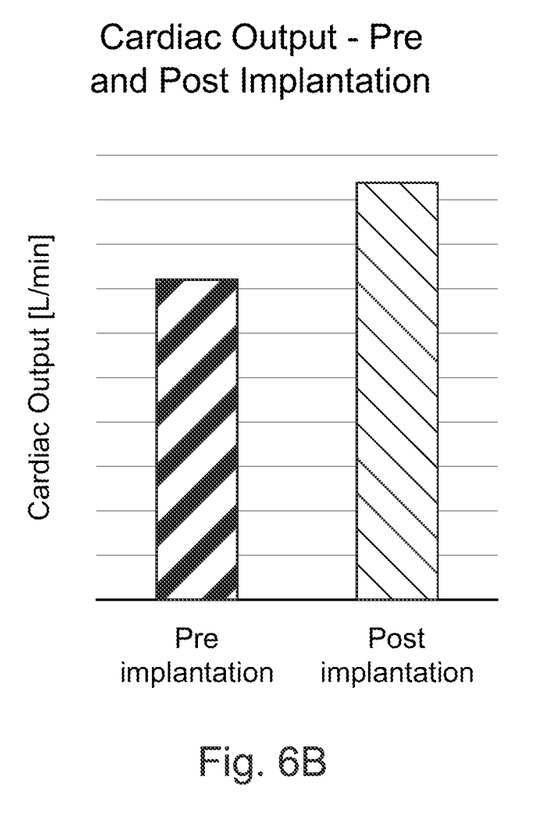

FIGS. 6A-B are charts illustrating physiological improvements with respect to post-implantation studies It is particularly noteworthy that in some embodiments of the present disclosure, direction of blood flow, either or both of entry and exit, need not be in specified (e.g., single) directions. For example, in some embodiments, blood need not flow into the device from one direction and then exit in another, e.g., perpendicular flow out of the device relative to the blood flow into the device. In some embodiments, the relatively small angle between the blood entrance and exit directions provides a greater efficacy to patients.

Specifically, rapid changes in flow direction, mainly due to the geometry of a blood vessel (or device in which blood flows through) can lead to turbulent flow and flow separation. Turbulence is a non-efficient form of fluid flow, characterized by rapidly changing pressure and velocity. In the physiological setting, turbulent flow prevents blood from moving in its natural course and will result in a decreased flux of blood across a given cross-sectional area. While a reduction in the blood supply rate can be overcome by an increase in blood pressure/velocity, since turbulence is directly influenced by the velocity of the fluid, an increase in blood velocity will result in yet more turbulence, and so on.

Moreover, since flow separation (when a fluid pulls away from the wall resulting in a region that includes a reduced flowrate associated therewith), is a common occurrence in blood vessel bifurcations, aneurisms, narrowing and other blood flow interferences, the blood in the slow-flow region typically forms a recirculation pattern in which the blood is trapped within that area (i.e., it is trapped within the recirculation zone since the blood cannot overcome the flowing fluid pressure to reenter the mainstream flow). In-general, this occurs when the angle between the main fluid flow direction and the wall is relatively large.

Accordingly, in some embodiments of the present disclosure, the valve/valves comprising one or more flaps/covers/blocking members and one or more openings, is/are configured to open in such a manner so as to permit blood to exit the tubular member (i.e., the device) in a flow direction which is relatively close to that of the natural flow within the vena cava. This results in the reduction or, in many cases, the elimination turbulence and flow separation, in comparison to devices that mandate sudden changes in blood flow direction.

It is also worth noting that the tricuspid valve opens during diastole for a duration of typically fractions of a second. To this end, the amount of blood that should enter the right ventricle through the tricuspid valve within every diastole typically exceeds 50 milliliters. In-addition, the pressure gradient (which is the blood flow driving force) across the tricuspid valve during diastole is only a few millimeters of Mercury, typically less than 10 mmHg. Thus, the tricuspid valve naturally allows a relatively large inflow rate under a small duration and driving force. Accordingly, the tricuspid valve (along with the mitral valve which experiences similar conditions) is typically is characterized by a large inflow cross-sectional area. Therefore, some embodiments obey this principal and provide a high flow rate valve(s) that constitute a relatively large opening area.

To this end, it is also particularly noteworthy that, in some embodiments, the tricuspid insufficiency device/device and included valve structure allows for changing pressure gradients (which can change significantly within a fraction of a second). Accordingly, such embodiments enable a significant amount (e.g., 50 ml or greater) of blood to flow across it, while prior art devices cannot. This is because in the remaining fraction(s) of a second that a valve is open, it must rapidly close to cease backflow through it, which is what occurs in some of the embodiments of the present disclosure (since the inflow of blood through such embodiments is driven by a pressure gradient of only a few mmHg). Such a flow in such a small duration through a 'slit valve' is not possible (for example).

Thus, in some embodiments, the disclosed device provides a high flow valve (which cannot be provided by a slit valve, for example), that allows a relatively large amount of blood to flow across it in a small amount of time, driven by a small pressure gradient (e.g., less than about 10 mmHg). Such is achieved, according to some embodiments, by configuring a device includes a valve or a plurality of valves that constitute a large (e.g., greater than 2 square cm) opening (open) area.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all structure, parameters, dimensions, materials, functionality, and configurations described herein are meant to be an example and that the actual structure, parameters, dimensions, materials, functionality, and configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the claims supported by the present disclosure, and equivalents thereto, inventive embodiments may be practiced otherwise than as specifically described and claimed. Inventive embodiments of the present disclosure are also directed to each individual feature, system, article, structure, material, kit, functionality, step, and method described herein. In addition, any combination of two or more such features, systems, articles, structure, materials, kits, functionalities, steps, and methods, if such are not mutually inconsistent, is included within the inventive scope of the present disclosure. Some embodiments may be distinguishable from the prior art for specifically lacking one or more features/elements/functionality (i.e., claims directed to such embodiments may include negative limitations).

Also, as noted, various inventive concepts are embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is currently claimed is:

1. A tricuspid insufficiency treatment device comprising:
a tubular member configured for implantation within a vena cava of a patient, the tubular member formed with a sidewall,
and
the device consisting of only three (3) valves arranged circumferentially along the sidewall, each valve comprising:
an opening formed in the sidewall, and
a blocking member comprising a flap or cover pivotally attached at or proximate a portion of a respective opening and arranged to block and unblock the opening during ventricular systole and ventricular diastole, respectively, such that the opening is unblocked in a direction opposite to the attachment of the flap or cover,
wherein
a first and a second valve of the at least three (3) valves are arranged along a first circumference at a first location between the ends of the tubular member,
a third valve of the three (3) valves is arranged on a second circumference spaced closer to one of the ends of the tubular member than that of the two (2) valves arranged on the first circumference.

2. The device of claim 1, wherein the tubular member and the blocking members of the valves form a closed cylindrical outer shape when each blocking member blocks a respective opening.

3. The device of claim 1, further comprising a covering configured to cover at least a portion of the tubular member.

4. The device of claim 3, wherein the covering:
does not cover the openings; or
is configured to additionally cover each blocking member.

5. The device of claim 1, wherein each of the first and second valves is hinged to the tubular member on opposite sides such that each blocking member opens away from the other blocking member.

6. The device of claim 5, wherein the third valve of the plurality of valves is hinged such that the blocking member opens away from the first and second blocking member.

7. The device of claim 1, wherein the tubular member includes an expandable stent having a plurality of cells, wherein each of the three valves correspond to a specific cell of the stent.

8. The device of claim 7, wherein:
at least one of the: each of the openings and each of the cells accommodating a respective opening includes a rhombus shape; or
the stent comprises a corona stent.

9. The device of claim 8, wherein the corona stent comprises a first inferior vena-cava (IVC) portion, a second superior vena-cava (SVC) portion, and a third central portion arranged between the IVC portion and the SVC portion.

10. The device of claim 1, wherein each blocking member includes a shape memory reinforcing wire therein or thereon.

11. The device of claim 10, wherein:
the reinforcing wire is arranged at or near at least a portion of the perimeter of the blocking member; or
the reinforcing wire is arranged at or near substantially the entire perimeter of the blocking member.

12. The device of claim 1, wherein a single side of the blocking member is attached to the tubular member.

13. The device of claim 12, wherein each blocking member is attached via suturing.

14. The device of claim 1, further comprising a skirt.

15. The device of claim 14, wherein:
the skirt is arranged on and attached to a portion of the tubular member and configured to at least one of preventing backflow from the right atrium (RA) into the inferior vena-cava (IVC), so as to redundify graft coverage of the IVC member, and preventing blockage of one or more hepatic veins;
the skirt comprises at least one of a fabric and a reinforcement; or
the skirt comprises a fabric and a reinforcement.

16. The device of claim 15, wherein the reinforcement comprises a shape memory wire.

17. The device of claim 16, wherein:
the wire is arranged along at least a portion of the perimeter of the skirt; or
the wire is arranged along a majority of the perimeter of the skirt.

18. The device of claim 3, wherein the covering is attached to the tubular member and/or stent via a plurality of sutures.

19. The device of claim 1, wherein the tubular member includes a longitudinal axis, and wherein at least one of the plurality of valves, or the device as a whole, is configured so as to cause substantially all the blood flowing out therefrom to flow in a non-perpendicular direction relative to at least the longitudinal axis and the vena cava.

20. A tricuspid insufficiency treatment device comprising:
a tubular member configured for implantation within a vena cava of a patient, the tubular member formed with a sidewall,
and
at least three (3) valves arranged in a single adjacent grouping along the sidewall, each valve comprising:
an opening formed in the sidewall, and
a blocking member comprising a flap or cover pivotally attached at or proximate a portion of a respective opening and arranged to block and unblock the opening during ventricular systole and ventricular diastole, respectively, such that the opening is unblocked in a direction opposite to the attachment of the flap or cover,
wherein each of the valves is hinged to the tubular member along different sides such that each blocking member opens away and in a different direction from each of the other blocking members.

21. The device of claim 20, wherein the at least three valves consisits of only three valves.

22. A tricuspid insufficiency treatment device comprising:
a tubular member configured for implantation within a vena cava of a patient, the tubular member formed with a sidewall,
and
a centralized grouping of at least three (3) valves arranged along the sidewall, each valve comprising:
an opening formed in the sidewall, and
a blocking member comprising a flap or cover pivotally attached at or proximate a portion of a respective opening and arranged to block and unblock the opening during ventricular systole and ventricular diastole, respectively, such that the opening is unblocked in a direction opposite to the attachment of the flap or cover,
wherein
the tubular member comprises an expandable stent having a plurality of cells,
each of the plurality of cells includes a first rhombus shape,
each opening for each of the at least three valves correspond to a specific respective cell of the stent, and
the blocking member includes a second rhombus shape that corresponds to the first rhombus shape.

23. The device of claim 22, wherein the at least three valves consists of only three valves.

24. A tricuspid insufficiency treatment device comprising:
a tubular member configured for implantation within a vena cava of a patient, the tubular member formed with a sidewall,
and
at least three (3) valves arranged circumferentially along the sidewall, each valve comprising:
an opening formed in the sidewall, and
a blocking member comprising a flap or cover pivotally attached at or proximate a portion of a respective opening and arranged to block and unblock the opening during ventricular systole and ventricular diastole, respectively, such that the opening is unblocked in a direction opposite to the attachment of the flap or cover,
wherein each blocking member includes a length of shape reinforcing wire arranged and running only along substantially the entire the perimeter thereof.

25. The device of claim 24, wherein the at least three valves consists of only three valves.

* * * * *